(12) United States Patent
Johnston et al.

(10) Patent No.: US 9,255,912 B2
(45) Date of Patent: Feb. 9, 2016

(54) MONOLITHIC FBAR-CMOS STRUCTURE SUCH AS FOR MASS SENSING

(75) Inventors: Matthew Johnston, New York, NY (US); Kenneth Shepard, Ossining, NY (US); Ioannis Kymissis, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 603 days.

(21) Appl. No.: 13/283,670

(22) Filed: Oct. 28, 2011

(65) Prior Publication Data

US 2012/0164753 A1 Jun. 28, 2012

Related U.S. Application Data

(63) Continuation-in-part of application No. PCT/US2010/032976, filed on Apr. 29, 2010.

(60) Provisional application No. 61/173,866, filed on Apr. 29, 2009, provisional application No. 61/215,611, filed on May 7, 2009, provisional application No. 61/531,993, filed on Sep. 7, 2011.

(51) Int. Cl.
*G01N 29/24* (2006.01)
*G01N 29/02* (2006.01)
(Continued)

(52) U.S. Cl.
CPC ............ *G01N 29/245* (2013.01); *G01N 29/022* (2013.01); *G01N 29/036* (2013.01); *H03B 5/364* (2013.01); *G01N 2291/0255* (2013.01);
(Continued)

(58) Field of Classification Search
CPC . G01N 29/245; G01N 29/036; G01N 29/022; H03B 5/364; H03H 9/545
See application file for complete search history.

(56) References Cited

U.S. PATENT DOCUMENTS

| 5,872,493 | A  | * | 2/1999 | Ella ............................... 333/191 |
| 7,221,242 | B2 | * | 5/2007 | Asai et al. ...................... 333/187 |

(Continued)

FOREIGN PATENT DOCUMENTS

| CN | 1449110 A | 10/2003 |
| CN | 1652458 A | 8/2005 |

(Continued)

OTHER PUBLICATIONS

"Canadian Application Serial. No. 2,760,508, Amendment filed Oct. 28, 2011", 6 pgs.

(Continued)

*Primary Examiner* — Melanie Y Brown
(74) *Attorney, Agent, or Firm* — Baker Botts L.L.P.

(57) ABSTRACT

An apparatus comprises a thin-film bulk acoustic resonator such as including an acoustic mirror, a piezoelectric region acoustically coupled to the acoustic mirror, and first and second conductors electrically coupled to the piezoelectric region. In an example, an integrated circuit substrate can include an interface circuit connected to the first and second conductors of the resonator, the integrated circuit substrate configured to mechanically support the resonator. An example can include an array of such resonators co-integrated with the interface circuit and configured to detect a mass change associated with one or more of a specified protein binding, a specified antibody-antigen coupling, a specified hybridization of a DNA oligomer, or an adsorption of specified gas molecules.

25 Claims, 10 Drawing Sheets

(51) Int. Cl.
*G01N 29/036* (2006.01)
*H03B 5/36* (2006.01)
*H03H 9/17* (2006.01)
*H03H 9/54* (2006.01)

(52) U.S. Cl.
CPC .. *G01N2291/0256* (2013.01); *G01N 2291/045* (2013.01); *G01N 2291/0426* (2013.01); *H03H 9/175* (2013.01); *H03H 9/545* (2013.01); *Y10T 29/42* (2015.01)

(56) References Cited

U.S. PATENT DOCUMENTS

| | | | |
|---|---|---|---|
| 8,525,619 | B1 | 9/2013 | Olsson et al. |
| 2003/0015941 | A1 | 1/2003 | Nakatani et al. |
| 2003/0199105 | A1 | 10/2003 | Kub et al. |
| 2004/0135144 | A1 | 7/2004 | Yamada et al. |
| 2006/0125489 | A1 | 6/2006 | Feucht et al. |
| 2006/0137453 | A1* | 6/2006 | Wu et al. ................. 73/581 |
| 2006/0139122 | A1* | 6/2006 | Asai ................. H03H 3/02 333/133 |
| 2006/0185139 | A1 | 8/2006 | Larson, III et al. |
| 2006/0202779 | A1 | 9/2006 | Fazzio et al. |
| 2006/0214747 | A1 | 9/2006 | Lakin |
| 2007/0007851 | A1 | 1/2007 | Loebl et al. |
| 2007/0210349 | A1* | 9/2007 | Lu et al. ................. 257/252 |
| 2011/0027930 | A1* | 2/2011 | El-Gamal et al. ............... 438/51 |

FOREIGN PATENT DOCUMENTS

| | | |
|---|---|---|
| CN | 101246162 A | 8/2008 |
| EP | 1959568 A1 | 8/2008 |
| WO | WO-0068419 A2 | 11/2000 |
| WO | WO-2008101646 A1 | 8/2008 |
| WO | WO-2010127122 A1 | 11/2010 |

OTHER PUBLICATIONS

"Canadian Application Serial No. 2,760,508, Office Action mailed Feb. 14, 2013", 2 pgs.
"Canadian Application Serial No. 2,760,508, Response filed Aug. 14, 2013 to Office Action mailed Feb. 14, 2013", 14 pgs.
"Chinese Application Serial No. 201080018971.9, Office Action mailed Mar. 20, 2014", w/English translation, 6 pgs.
"Chinese Application Serial No. 201080018971.9, Office Action mailed Jul. 2, 2013", w/English translation, 18 pgs.
"Chinese Application Serial No. 201080018971.9, Office Action mailed Dec. 5, 2013", w/English translation, 19 pgs.
"Chinese Application Serial No. 201080018971.9, Response filed Feb. 20, 2014 to Office Action mailed Dec. 5, 2013", w/English claims, 11 pgs.
"Chinese Application Serial No. 201080018971.9, Response filed Nov. 18, 2013 to Office Action mailed Jul. 2, 2013", w/English claims, 10 pgs.
"European Application Serial No. 10770334.0, Extended European Search Report mailed Apr. 24, 2014", 6 pgs.
Abdolvand, Reza, et al., "ZNO-on-nanocrystalline diamond lateral bulk acoustic resonators", IEEE 20th International Conference on Micro Electro Mechanical Systems, 2007. MEMS., (2007), 795-798.
Brederlow, R., et al., "Biochemical sensors based on bulk acoustic wave resonators", IEEE International Electron Devices Meeting, 2003. IEDM '03 Technical Digest., (2003), 32.7.1-32.7.3.
Clark, J. R, et al., "High-Q VHF micromechanical contour-mode disk resonators", Technical Digest. International Electron Devices Meeting, 2000. IEDM '00., (2000), 493-496.
Gabl, R, et al., "First results on label-free detection of DNA and protein molecules using a novel integrated sensor technology based on gravimetric detection principles", Biosensors and Bioelectronics, 19(6), (Jan. 15, 2004), 615-620.
Lee, Jae Bin, et al., "Deposition of ZnO thin films by magnetron sputtering for a film bulk acoustic resonator", Thin Solid Films, 435(1-2), (Jul. 1, 2003), 179-185.
Otis, Brian P, et al., "A 300μW 1.9GHz CMOS Oscillator Utilizing Micromachined Resonators", Proceedings of the 28th European Solid-State Circuits Conference, 2002. ESSCIRC 2002., (2002), 151-154.
Piazza, G., "MEMS Resonators for Frequency Control and Sensing Applications", [Online]. Retrieved from the Internet: <URL: http://www.ifcs-eftf2011.org/sites/ifcs-eftf2011.org/files/editor-files/Slides_Piazza.pdf>, (Accessed Apr. 30, 2014), 104 pgs.
Rinaldi, M., et al., "AIN contour-mode resonators for narrow-band filters above 3 GHz", IEEE International Frequency Control Symposium, 2009 Joint with the 22nd European Frequency and Time forum., (2009), 70-74.
"International Application Serial No. PCT/US10/32976, Search Report mailed Aug. 4, 2010", 8 pgs.
"International Application Serial No. PCT/US10/32976, Written Opinion mailed Aug. 4, 2010", 8 pgs.
Johnston, Matthew L., et al., "FBAR-CMOS Oscillator Array for Mass-Sensing Applications", IEEE Sensors Journal, vol. 10, No. 6, (Jun. 2010), 1042-1047.

\* cited by examiner

MONOLITHIC FBAR-CMOS STRUCTURE SUCH AS FOR MASS SENSING

CLAIM OF PRIORITY

1. This application is a continuation-in-part under 35 U.S.C. 111(a) of International Application No. PCT/US2010/032976, filed Apr. 29, 2010 and published as WO 2010/127122 on Nov. 4, 2010, which claimed priority under 35 U.S.C. 119(e) to U.S. Provisional Patent Application Ser. No. 61/173,866, filed on Apr. 29, 2009, and U.S. Provisional Patent Application Ser. No. 61/215,611, filed on May 7, 2009, priority to both of which is hereby presently claimed, and both of which applications are hereby incorporated by reference herein in their respective entireties.

2. This application also claims priority under 35 U.S.C. 119(e) to U.S. Provisional Patent Application Ser. No. 61/531,993, filed Sep. 7, 2011, which application is hereby incorporated by reference herein in its entirety.

STATEMENT REGARDING FEDERALLY SPONSORED RESEARCH OR DEVELOPMENT

This invention was made with government support under award number U01ES016074 from the National Institute of Environmental Health Sciences or the National Institutes of Health. The government has certain rights in this invention.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the drawings and photos that form a part of this document: Copyright 2010, The Trustees of Columbia University in the City of New York, All Rights Reserved.

BACKGROUND

Ultra-high-precision mass sensing can be an important detection method such as for biomolecular and chemical detection. Detecting molecules by mass need not require chemical or fluorescent labeling, which can allow for simplified detection protocols and for sensing in systems adversely affected by labeling. For example, the limited cross reactivity of fluorescently labeled generic binders can limit the specificity of a protein assay, such as used for analyzing or characterizing various cells, biomarkers, or autoimmune diseases, among others. Additionally, use of unbound labeled reporters can also have limitations, such as preventing real-time detection and quantification of binding events, as such unbound reporters must generally be washed away prior to optical interrogation.

SUMMARY

Effective treatment of acute coronary syndromes generally relies on rapid and accurate diagnosis of such syndromes. Therapeutic benefit generally falls off sharply in the hours following an attack. Such diagnosis or risk stratification can include detecting or otherwise analyzing one or more cardiac biomarkers. In an example, such cardiac biomarkers can include one or more of cardiac troponins, myoglobin, or creatine kinase.

Clinical guidelines can specify a turnaround time of 30-60 minutes or less time for cardiac biomarker measurement, and generally available facilities and techniques can rarely achieve such a turnaround. The present inventors have recognized, among other things, that a rapid point-of-care (POC) cardiac test platform can improve (e.g., reduce) such turnaround time, such as using information provided by a sensor technology as shown and described in this document. Such a test platform can include one or more integrated circuits or one or more other microelectronic devices such as for POC protein quantification, or for use in other detection or diagnostic applications.

The sensor technology can use integrated circuit (IC) technology that has otherwise been used in the fabrication of low-cost microprocessors. Such IC technology can be used for non-computational applications, such as in biosensing or for other bioelectronic uses. In an example, a custom IC substrate can be combined with a resonant sensor, or an array of resonant sensors (e.g., two or more, to dozens or more), such as to enable low-cost, multiplex protein quantification.

In an example, such a sensor comprises a thin-film bulk acoustic resonator (FBAR) that can include a micron-scale device providing a resonant frequency that can change as molecules attach to its surface. In an example, this can provide a scaled-down microbalance, which can allow for very sensitive detection, such as of protein binding, gas adsorption, DNA hybridization, or for detection of other species. In an example, such sensors can be built directly atop or otherwise cointegrated on a commonly-shared IC microchip, such as to create a new class of self-contained, disposable biochemical assay devices. Such examples can provide improvements over non-integrated sensors via one or more of: a sensitivity or a coefficient of variation (CV); a capability to multiplex sampling of target analytes; a decreased hardware cost such as to provide a disposable assembly; or a decreased sample volume.

For example, use of such sensors can be targeted at clinical stratification of acute coronary syndromes, which can be extended to include one or more additional cardiac biomarkers or diagnostic differentiators of infection, pulmonary embolism, or one or more other confounding diagnoses. In an example, the technology described herein can lay the foundation for a multitude of multiplexed POC applications, such as in infectious disease, cancer diagnostics, autoimmune disease monitoring, or in-the-field medical testing.

This document presents, among other things, a monolithic, integrated solidly-mounted thin-film bulk acoustic wave resonator (FBAR) mechanically and electrically coupled to an active integrated circuit, such as a complementary metal-oxide-semiconductor (CMOS) integrated circuit. Such a FBAR-CMOS sensor, or a monolithic array of such sensors, can be used for mass sensing applications. In contrast to externally coupled FBAR structures or other types of resonant mass sensors, the present inventors have recognized that an integrated array of sensors can be built directly above or otherwise cointegrated with active drive and readout circuitry. In an FBAR-CMOS array, one or more individual FBAR mass sensors included in the array can be functionalized in a specified manner, such as for capturing a specific protein, nucleic acid, or gas molecule. An array of such functionalized sensors can allow simultaneous, multiplexed, high-sensitivity measurement of multiple targets (e.g., detection or measurement of multiple, different, species) on a single (e.g., monolithic) sensor chip. In other examples, one or more FBAR-CMOS devices can be used as a filter, oscillator, or transformer, such as for microwave or solid-state power conversion applications, among others.

The monolithic, solidly-mounted FBAR resonator apparatus can comprise a piezoelectric zinc oxide resonator atop a mechanically isolating acoustic mirror. The mirror can function as a mechanical analog to an optical Bragg stack, as acoustic waves are reflected back into the resonator through quarter-wavelength layers and constructive interference. Such reflection by the isolating acoustic mirror can inhibit or prevent coupling of acoustic energy into the substrate below the resonator.

In Example 1, an apparatus can include a thin-film bulk acoustic resonator comprising an acoustic mirror, a piezoelectric region acoustically coupled to the acoustic mirror, a first conductor electrically coupled to the piezoelectric region, a second conductor electrically coupled to the piezoelectric region and electrically insulated from the first conductor. In Example 1, the apparatus optionally includes an integrated circuit substrate including an interface circuit, the first and second conductors electrically coupled to the interface circuit, the integrated circuit substrate configured to mechanically support the resonator, the acoustic mirror configured to inhibit or prevent coupling of acoustic energy from the piezoelectric region to the integrated circuit substrate at or near a resonant frequency of the thin-film bulk acoustic resonator.

In Example 2, the subject matter of Example 1 optionally includes a piezoelectric region comprising zinc oxide.

In Example 3, the subject matter of any one or more of Examples 1-2 optionally includes an acoustic mirror comprising alternating layers of tungsten and silicon dioxide.

In Example 4, the subject matter of any one or more of Examples 1-3 optionally includes an interface circuit comprising a CMOS circuit, and a resonator located on a top surface of the integrated circuit.

In Example 5, the subject matter of any one or more of Examples 1-4 optionally includes an oscillator including the acoustic resonator and at least a portion of the interface circuit.

In Example 6, the subject matter of any one or more of Examples 1-5 optionally includes an operating frequency of the oscillator determined at least in part by a mass loading the piezoelectric region.

In Example 7, the subject matter of any one or more of Examples 1-6 optionally includes a resonator comprising a sensing surface configured to detect at least one of a specified protein binding, a specified antibody-antigen coupling, a specified hybridization of a DNA oligomer, or an adsorption of specified gas molecules.

In Example 8, the subject matter of any one or more of Examples 1-7 optionally includes a sensing surface functionalized to adsorb gas molecules.

In Example 9, the subject matter of any one or more of Examples 1-8 optionally includes a sensing surface including an immobilized antibody, an antibody fragment, or a nucleic acid probe.

In Example 10, the subject matter of any one or more of Examples 1-9 optionally includes a sensing surface configured to increase in mass in response to at least one of a specified protein binding, a specified antibody-antigen coupling, a specified hybridization of a DNA oligomer, or an adsorption of specified gas molecules.

In Example 11, the subject matter of any one or more of Examples 1-10 optionally includes an oscillator configured to operate using a shear mode of mechanical oscillation of the resonator.

In Example 12, the subject matter of any one or more of Examples 1-11 optionally includes an oscillator configured to oscillate at the specified operating frequency when the apparatus is in contact with or surrounded by a liquid medium.

In Example 13, the subject matter of any one or more of Examples 1-12 optionally includes an integrated circuit comprising a frequency counter coupled to the oscillator and configured to provide information indicative of an oscillation frequency of the oscillator.

In Example 14, an apparatus includes a thin-film bulk acoustic resonator array, each resonator comprising an acoustic mirror, a piezoelectric region acoustically coupled to the acoustic mirror, a first conductor electrically coupled to the piezoelectric region, a second conductor electrically coupled to the piezoelectric region and electrically insulated from the first conduct. In this example, the apparatus optionally includes an integrated circuit substrate including an interface circuit, the first and second conductors of each resonator electrically coupled to the interface circuit, the integrated circuit substrate configured to mechanically support the resonator array, and each respective acoustic mirror is configured to reduce or inhibit coupling of acoustic energy from the respective piezoelectric region into the integrated circuit substrate at or near a resonant frequency of the respective thin-film bulk acoustic resonator including the respective acoustic mirror. In this example, the array optionally includes an array of oscillators, each oscillator including at least one acoustic resonator and at least a portion of the interface circuit.

In Example 15, the subject matter of any one or more of Examples 1-14 optionally includes at least one oscillator in the array comprising a resonator having a sensing surface that is configured to detect at least one of a specified protein binding, a specified antibody-antigen coupling, a specified hybridization of a DNA oligomer, or an adsorption of specified gas molecules.

In Example 16, the subject matter of any one or more of Examples 1-15 optionally includes an integrated circuit comprising a frequency counter coupled to at least one oscillator included in the array, and configured to provide information indicative of an oscillation frequency of the at least one oscillator.

In Example 17, a method includes forming a thin-film bulk acoustic resonator on an integrated circuit substrate, such as including forming an acoustic mirror configured to reduce coupling of acoustic energy from a piezoelectric region into the integrated circuit substrate at or near a resonant frequency of the thin-film bulk acoustic resonator, forming a piezoelectric region acoustically coupled to the acoustic mirror, and electrically coupling a first conductor between a piezoelectric region and an interface circuit included in the integrated circuit substrate, electrically coupling a second conductor between the piezoelectric region and the interface circuit included in the integrated circuit substrate.

In Example 18, the subject matter of any one or more of Examples 1-17 optionally includes electrically coupling the first and second conductors to the piezoelectric region including depositing a metal.

In Example 19, the subject matter of any one or more of Examples 1-18 optionally includes depositing tungsten.

In Example 20, the subject matter of any one or more of Examples 1-19 optionally includes forming an acoustic mirror including forming alternating layers of silicon dioxide and tungsten on a top surface of the integrated circuit substrate.

In Example 21, the subject matter of any one or more of Examples 1-20 optionally includes forming an array of thin-film bulk acoustic resonators on the integrated circuit substrate.

In Example 22, the subject matter of any one or more of Examples 1-21 optionally includes providing a sensing surface on the resonator to detect at least one of a specified protein binding, a specified antibody-antigen coupling, a specified hybridization of a DNA oligomer, or an adsorption of specified gas molecules.

In Example 23, the subject matter of any one or more of Examples 1-22 optionally includes functionalizing a sensing surface on the resonator to promote adsorption of specified gas molecules.

In Example 24, the subject matter of any one or more of Examples 1-23 optionally includes providing an oscillator using the resonator and at least a portion of the interface circuit, an operating frequency of the oscillator determined at least in part by a mass loading the piezoelectric region.

In Example 25, the subject matter of any one or more of Examples 1-24 includes providing a frequency counter configured to measure information indicative of an oscillation frequency of the oscillator, using at least a portion of the interface circuit.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
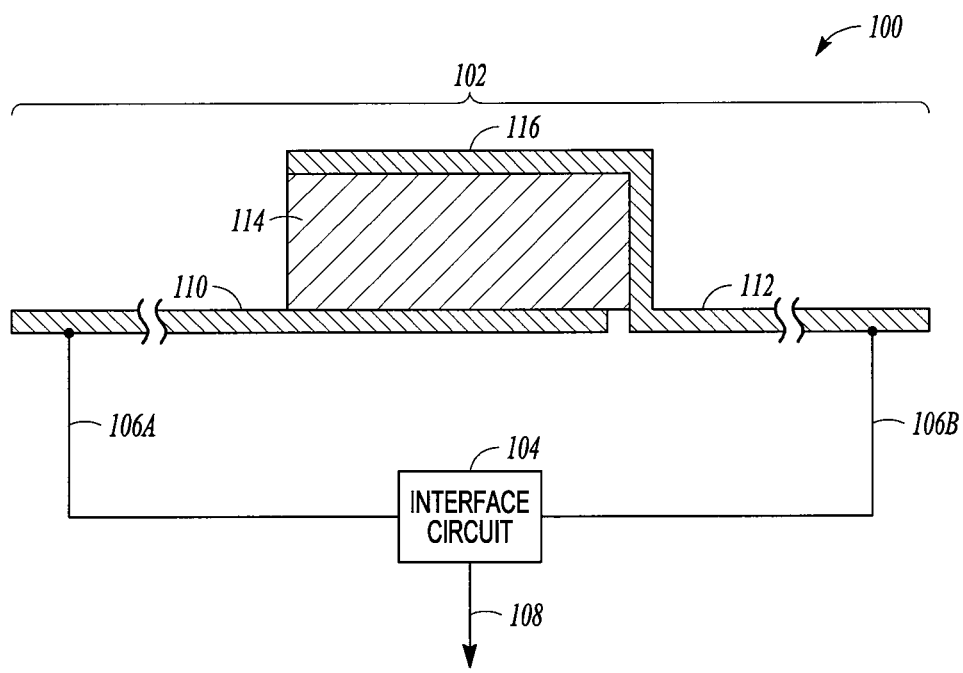
FIG. 1 illustrates generally an example of a side view of a section of a thin-film bulk acoustic resonator (FBAR) and an interface circuit.

In gravimetric biomolecular detection, a specific antibody, antibody fragment, or nucleic acid probe can be immobilized on the surface of a mechanical sensor, such as a mechanical resonator. Target molecules can bind to the immobilized probe, further increasing the bound mass. In an example, mass sensing can be performed by electrically monitoring the resonant frequency of a lightweight, high-Q mechanical resonator, such as in contact with such bound material to be measured. An increase in mass at the resonator surface causes an overall decrease in the mechanical, and hence electrical, resonant frequency of the loaded system, and this frequency can be measured and used to determine the mass addition, such as in real-time as the bound material accumulates, and without requiring fluorescent labels.

Quartz crystal microbalances (QCMs) have been used to detect antibodies and antigens, such as at sensitivities comparable to traditional labeled immunoassays. However, in a QCM, the resonant frequency can be limited by the thickness of self-supporting quartz (e.g., in the megaHertz range). In a resonant mass sensor, the extent of frequency change per unit mass can be related to the square of the resonant frequency, thus limiting the QCM's sensitivity. Moreover, centimeter-scale QCM sensors can preclude high-density integration, which can limit QCM sensors to applications involving a relatively small number of target analytes.

In contrast, the present inventors have recognized thin-film bulk acoustic resonators (FBARs) can allow for sensitivities orders of magnitude higher than other resonant structures, such as QCMs, since FBARs can have resonant frequencies in range of hundreds of megaHertz to several gigaHertz. For example, an individual FBAR can be interfaced with active CMOS components such as through wire-bonding or flip-chip connection approaches (e.g., an "external" coupling approach). But, such an external coupling can prevent more than one or two resonators from being integrated within a single chip. Thus, the present inventors have also recognized that monolithically integrating an FBAR along with active CMOS components can allow for significantly smaller size than the external coupling approach. Thus, an integrated array of FBARs can be built directly above active drive and readout circuitry (e.g., including CMOS circuitry). In an array of such mass sensors, one or more individual mass sensors included in the array can be functionalized in a specified manner, such as for detecting binding of a specified protein, a specific antibody-antigen coupling, a specified hybridized DNA oligomer, or specified adsorbed gas molecules. An array of such functionalized sensors can allow simultaneous, multiplexed, high-sensitivity measurement of multiple targets (e.g., detection or measurement of multiple, different, species) on a single monolithic sensor assembly.

In an example, the FBAR-CMOS sensor, or an array, can be used for an immunoassay for industrial, medical, or agricultural use, among others, such as for identifying pathogens, contaminents, allergans, toxins, or other compounds. In another example, the FBAR-CMOS sensor, or an array, can be used as a mass-sensor for gene-expression, either statically (e.g., at an endpoint of a reaction) or in real-time. In yet another example, the FBAR-CMOS sensor, or an array, can be used for gas sensing or air sample monitoring, such as in response to surface modification (e.g., adsorption or vapor condensation) on a sensing surface included as a portion of the FBAR-CMOS sensor or array. In other examples, FBAR resonators can also be used in microwave circuit applications. Such FBAR resonators can have relatively sharp resonances at high frequency, such as for use in filters, oscillators, or as transformers (e.g., transformers of voltage or impedance, etc.).

FIG. 1 illustrates generally an example of a side view 100 of a section of a thin-film bulk acoustic resonator (FBAR) 102, including a sensing surface 116 electrically connected to a first electrode 112, a piezoelectric region 114, a second electrode 110, and an interface circuit 104. In an example, the interface circuit 104 can be electrically connected to the FBAR 102 such as using a first electrical connection 106A and a second electrical connection 106B, such as including a metal layer included in an integrated circuit. In an example, one or more of the first or second electrodes 112, 110 can include tungsten, such as sputtered or deposited on an integrated circuit substrate. In another example, one or more other metals can be used, such as gold, silver, etc. In the example of FIG. 1, the interface circuit 104 can provide an output 108, such as carrying a voltage, current, or other signal indicative of an oscillation frequency. In an example, the combination of the FBAR 102 and the interface circuit 104 can provide an oscillator, such as including an operating frequency determined at least in part by a mass bound to or otherwise loading the sensing surface 116.

In an illustrative example, the height of the FBAR 102 can be about 2 micrometers, and the width of the sensing surface 116 can be about 100 micrometers. In an example, the piezoelectric region 114 can include Zinc Oxide (ZnO), lead zirconate titanate (PZT), aluminum nitride, or one or more other piezopolymers, piezoceramics, or other piezoelectric materials. In an example, the FBAR 102 can resonate using a shear mode of oscillation, such as at a resonant operating frequency in the range of about 500 megaHertz, or at a resonant frequency of 2 gigaHertz or more. In an example, such as shown in FIG. 3, FIGS. 4A through 4I, and FIGS. 5 through 6, a mechanical isolator, such as an acoustic mirror, can inhibit or prevent coupling of acoustic energy at or near the resonant operating frequency of the FBAR 102 into the surrounding substrate, such as to provide a higher quality factor "Q" (e.g., including a more sharply-peaked resonant operating frequency as compared to using one or more other resonator structures such as including a membrane or a cantilever).

Figure 2:
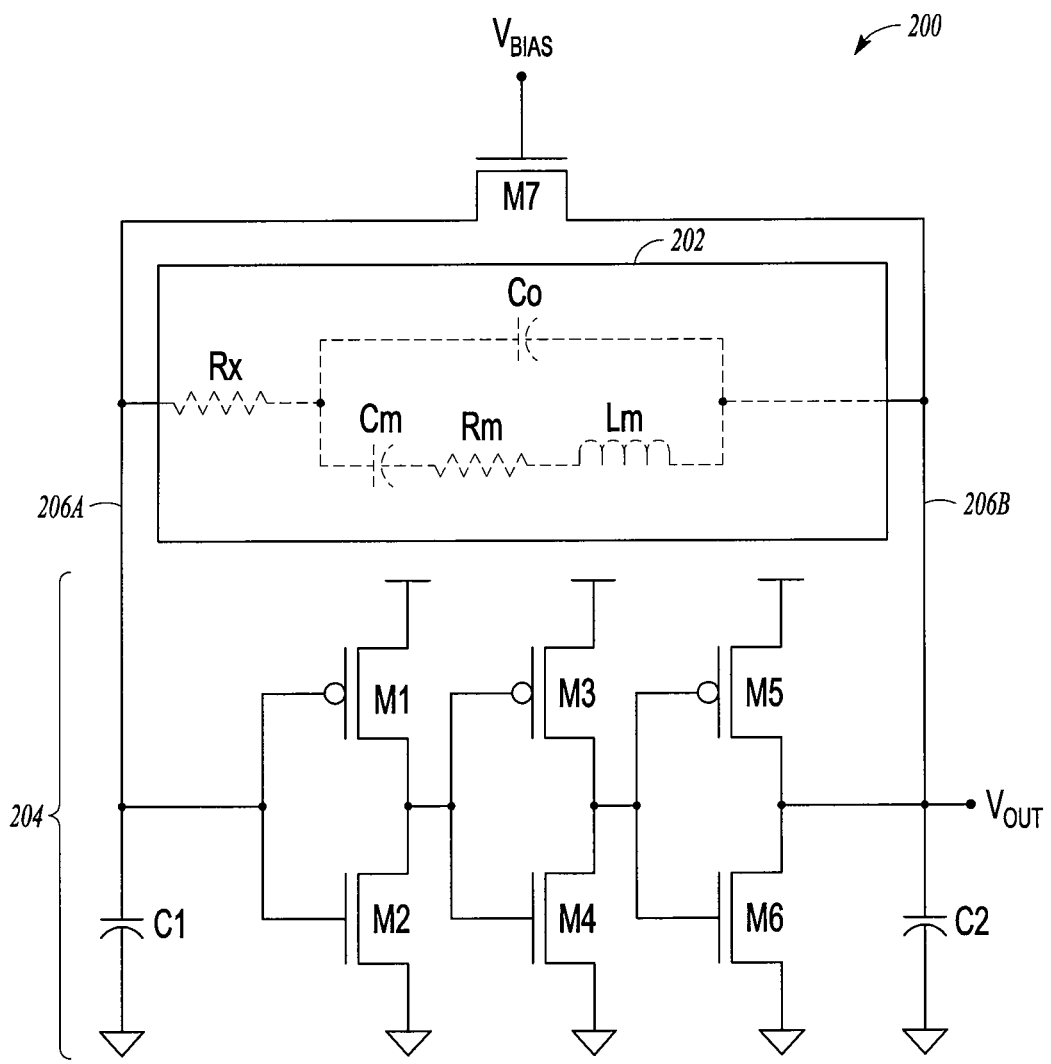
FIG. 2 illustrates generally an example of an oscillator circuit including an FBAR, and interface circuitry.

FIG. 2 illustrates generally an example of an oscillator circuit 200 including an FBAR 202, and an interface circuit including MOS transistors M1-M6. In an example, the circuit 200 of FIG. 2 can represent a single sensor such as included in an array of FBARs 202, such as a single sensor included in the 6×4 array shown in the examples of FIG. 6. In the example of FIG. 2, the FBAR 202 can be connected to an inverting CMOS amplifier 204, the amplifier 204 including the MOS transistors M1-M6 such as to form an integrated FBAR-CMOS oscillator circuit 200. The MOS transistors M1-M6 need not literally include a metal gate, instead using polysilicon or other conductive gate material, such as fabricated using a commercial 0.18 micrometer CMOS fabrication process. Similarly, in an example, a semiconductor material other than silicon, or an oxide other than silicon dioxide can be used to realize one or more of transistors M1-M6.

In FIG. 2, the oscillator circuit 200 can include a Pierce oscillator topology. For example, the inverting amplifier 204 can be implemented as three in-line CMOS inverters realized by the MOS transistors M1 through M6, such as to provide gain to overcome the FBAR material losses, sustaining oscillation. In the example of FIG. 2, a MOS transistor M7 can provide bias to MOS transistors M1 through M6. For example, transistor M7 can include a voltage-controlled gate, such as adjusted to balance biasing strength against oscillator loading. In an example, transistor M7 can be controlled by a voltage at a node $V_{BIAS}$, such as to calibrate the oscillator circuit or to otherwise accommodate variations in individual FBAR sensors due to design or fabrication variations, or other sources of variation. In an example, an output voltage at a node $V_{OUT}$ can be provided to a co-integrated or off-chip analog or digital frequency counter, such as to provide continuous monitoring or sampling of the output frequency of the oscillator 200 during specified intervals of operation (e.g., to measure a shift in frequency corresponding to an increased mass, or for one or more other uses).

In the example of FIG. 2, a first capacitor C1 and a second capacitor C2 can promote oscillator startup. For example, C1 and C2 can include metal-insulator-metal (MIM) capacitors that can be set to approximately equal values. Again, the term metal-insulator-metal need not refer literally to metal plates, as capacitors C1 and C2 can be co-integrated on the same monolithic CMOS integrated circuit as transistors M1 through M7. In an illustrative example, the FBAR 102 can be represented by an equivalent Butterworth-Van Dyke circuit, as shown in FIG. 2. In this illustrative example, Cm, Rm, and Lm can electrically represent the motional components of the FBAR, and Co, and Rx can represent the intrinsic electrical properties of the FBAR (e.g., the bulk properties of the piezoelectric material, such as ZnO, or properties of one or more other materials). In an example, the FBAR 102 can serve as a high-Q resonant tank circuit for the oscillator.

Figure 3:
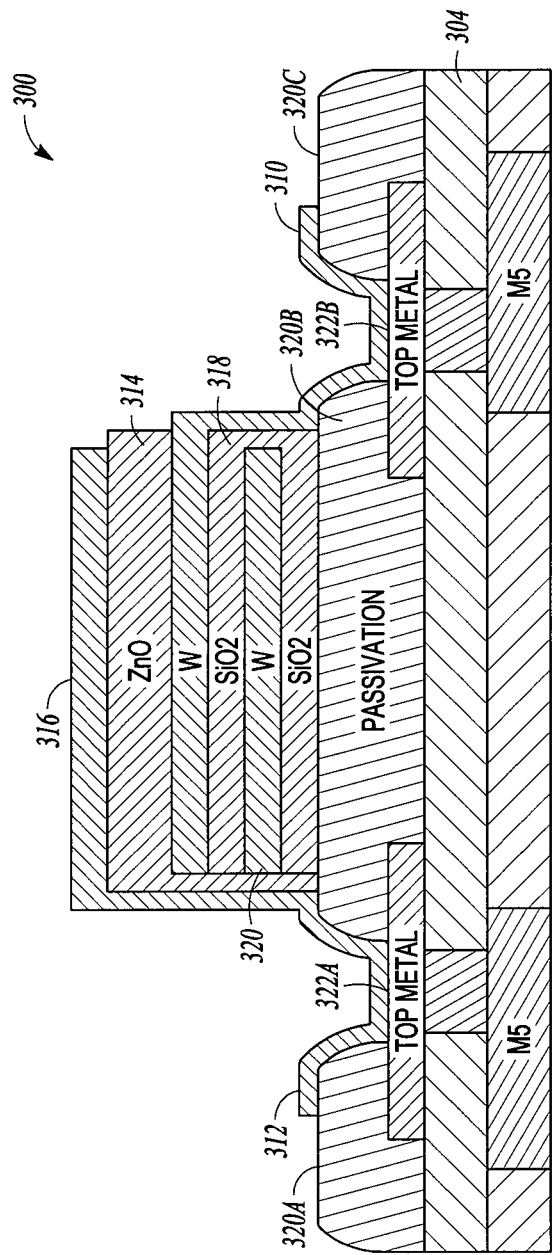
FIG. 3 illustrates generally an example of a side view of a section of a solidly-mounted FBAR including an acoustic mirror portion.

FIG. 3 illustrates generally an example of a side view of a section of a solidly-mounted FBAR 300 including an acoustic mirror portion. In FIG. 3, the FBAR 300 can be fabricated on top of a first, a second, and a third passivation region 320A through 320C of an integrated circuit, such as either a passive substrate 304 or an active integrated circuit substrate 304. In another example, the FBAR 300 can be fabricated on an integrated circuit without passivation regions 320A through 320C (e.g., such as in-line, prior to passivation, along with other processing during fabrication of the active circuitry portion of the sensor assembly). A first electrode 312 can be electrically connected to a first top metal layer region 322A of the integrated circuit, and a second electrode 310 can be electrically connected to a second top metal layer region 322B of the integrated circuit. The present inventors have also recognized that a solidly-mounted FBAR 300 structure can allow simple fabrication, such as described in FIGS. 4A through 4I, unlike other bulk acoustic wave structures, such as those including a membrane. For example, the FBAR 300, or an array of FBARs 300, can be built up via sequential deposition and patterning of each layer without requiring undercutting or sacrificial layer integration processes, such as might be used in fabricating other types of bulk acoustic wave structures.

In the example of FIG. 3, the FBAR 300 can include a sensing surface 316, such as formed by a portion of the first electrode 312. The sensing surface 316 can be coupled to a piezoelectric region 314 (e.g., ZnO or one or more other piezoelectric materials such as PZT or aluminum nitride). Unlike the example of FIG. 1, the FBAR 300 of FIG. 3 includes an acoustic mirror, such as to mechanically isolate the mechanically resonant portion of the FBAR 300 from the rest of the mechanically supporting substrate 304 (e.g., below the passivation regions 320A through 320C). Generally, a mechanical resonator can be mechanically isolated from its supporting substrate, such as to help avoid dissipating too much energy into its surroundings (which could dampen oscillation or likely prevent oscillation). In some examples, this mechanical isolation can be accomplished with an air gap, where the FBAR 300 structure can be implemented as a membrane or cantilever structure. In other examples, the isolation can be accomplished through a dielectric acoustic mirror. Such isolation can allow the FBAR 300 to operate with a sharply-peaked resonant response despite being solidly-mounted to the substrate 304. In the example of FIG. 3, one or more alternating layers of relatively high- and relatively low-acoustic-impedance material can be used, such as to provide a mechanical analog to a distributed Bragg reflector.

For example, one or more of an insulating layer 318, and a conductive layer 320 can each be about one-quarter of an acoustic wavelength thick, such as an acoustic wavelength in each respective material at or near a resonant operating frequency of the FBAR 300. The combination of alternating layers 318 and 320 (e.g., such as including more or fewer alternating layers than shown in the illustrative example of FIG. 3) can inhibit or prevent the mechanical coupling of acoustic energy into the substrate 304 in the region below the piezoelectric region 314, the sensing surface 316, and the second electrode 310. For example, the layers 318 and 320 can be sized and shaped to promote constructive interference of acoustic energy at or near the resonant operating frequency of the FBAR 300, at the interfaces between the layers 318 and 320, and between the electrode 310 and the piezoelectric region 314, reflecting a majority of acoustic energy back towards the piezoelectric region 314. In an illustrative example, the conductive layer 320 can be tungsten, and the insulating layer 318 can be silicon dioxide, or one or more other insulating materials. In FIG. 3, the second electrode 310 can also be used as the top layer in the acoustic mirror. However, in other examples, an insulator such as silicon dioxide can be used as the top functional layer of the mirror, such as including a deposited or sputtered thin-film conductive coating to provide the second electrode 310 (e.g., including a thin gold or silver layer, or other conductive material).

In an example, the sensing surface 316 can include or can be coated with gold, silicon dioxide, laminated parylene, or one or more other biologically compatible materials, such as in preparation for functionalization for subsequent detection of a change in mass associated with a specified protein binding, a specified antibody-antigen coupling, a specified hybridization of a DNA oligomer, or an adsorption of specified gas molecules, among others.

Figure 4A:
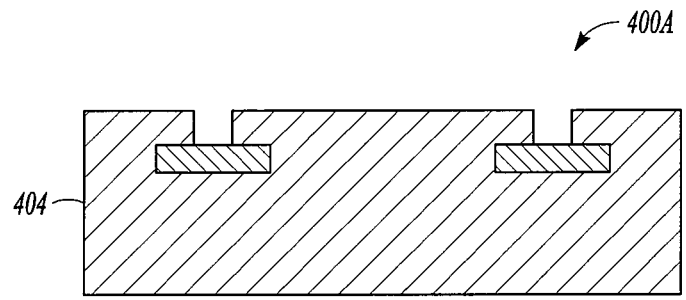
FIGS. 4A through 4I illustrate generally examples of post-CMOS fabrication of a monolithic thin-film bulk acoustic resonator (FBAR), such as included in array of FBAR-CMOS oscillators.

FIGS. 4A through 4I illustrate generally an example of post-CMOS fabrication of a monolithic thin-film bulk acoustic resonator (FBAR) 400, such as included in array of FBAR-CMOS oscillators. The fabrication processes of FIGS. 4A through 4I need not require specialized fabrication techniques or non-standard CMOS fabrication processes (e.g., such fabrication can include processing and materials similar to that used for commercial digital or mixed signal CMOS device fabrication). In FIG. 4A, the post-CMOS fabrication of the FBAR 400A can begin with a commercial integrated circuit substrate 404, such as including one or more openings in a passivation layer, exposing one or more metal regions. In an illustrative example, the integrated circuit substrate 404 can include an active CMOS substrate (e.g., an integrated circuit substrate including one or more active devices or circuits), such as fabricated using a commercial 0.18 μm foundry CMOS process, or using one or more other fabrication processes.

Figure 4B:
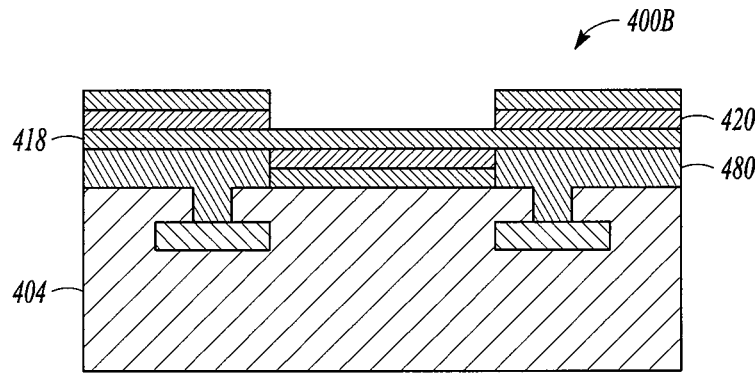

In FIG. 4B, the post-CMOS substrate 404 can be patterned, such as using a relatively thick photoresist layer (e.g., about 1 micrometers to 8 micrometers, or using another thickness). Then, alternating layers of silicon dioxide (e.g., about 750 nanometers thick) and tungsten (e.g., about 650 nanometers thick) can be formed on the substrate 404, such as by RF sputtering onto the patterned substrate, such as including a metal layer 420, and an insulating layer 418, similar to the layers discussed above in the example of the acoustic mirror of FIG. 3. In FIG. 4B, since the photoresist layer can be relatively thick, the exposure times can be increased correspondingly to compensate for pronounced edge and corner beads.

Figure 4C:
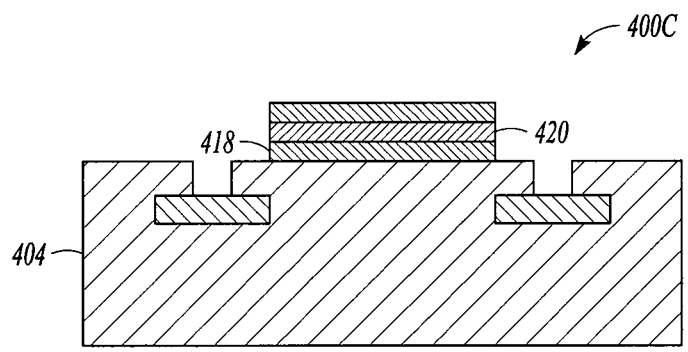
Figure 4D:
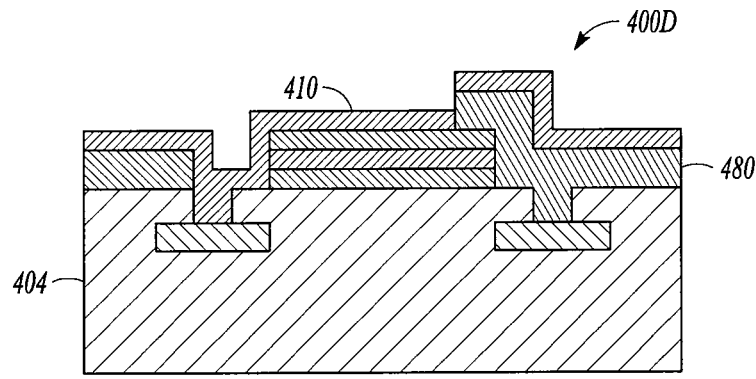
Figure 4E:
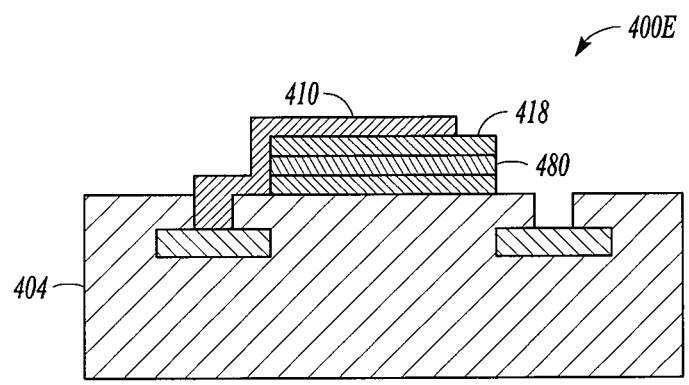

In FIG. 4C, the metal layer 420 and insulating layer 418 in the regions above the remaining photoresist can be lifted off (e.g., with ultrasonic assistance), or otherwise removed from the FBAR 400C, leaving behind the metal layer 420 and insulating layer 418, such as between the passivation openings in the substrate 404, on a working top surface of the substrate 404. In an illustrative example, the metal layer 420 and insulating layer 418 can form at least a portion of an acoustic mirror as discussed above in FIG. 3. In FIG. 4D, the FBAR 400D can again be patterned, and a top tungsten acoustic mirror layer 410 (or another conductive material) can be deposited or sputtered onto the exposed portions of the FBAR 400D above a working top surface region of the substrate 404. In an example, the top tungsten mirror layer 410 can also serve as the bottom electrode of the FBAR 400D, and this layer can connect to the top metal layer of the CMOS substrate such as through an opening in the passivation layer 404. In FIG. 4E, the unwanted portions of the tungsten mirror layer 410 can be lifted off or otherwise removed from the FBAR 400E.

Figure 4F:
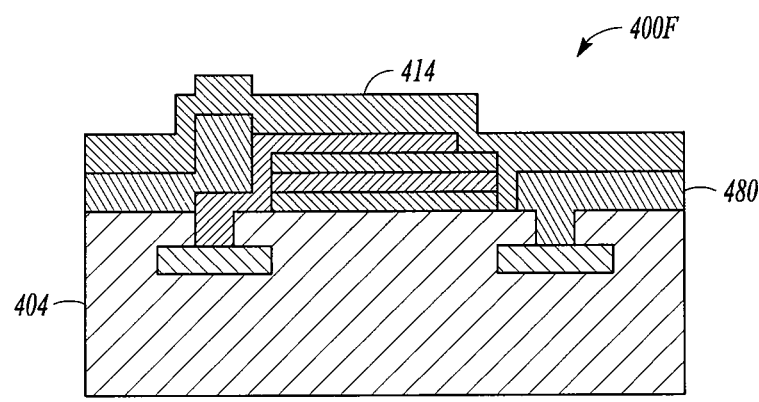
Figure 4G:
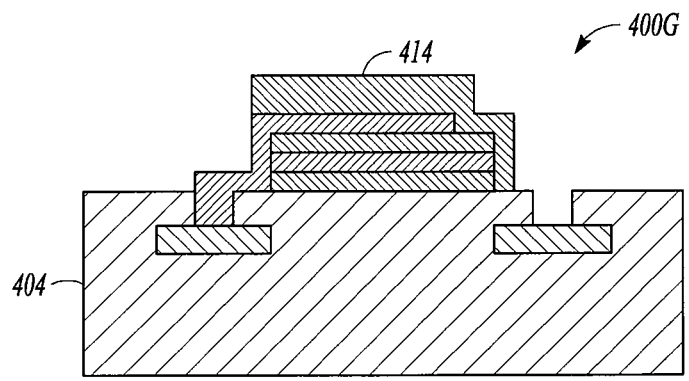

In FIG. 4F, the FBAR 400F can be patterned, and a piezoelectric region 414 can be formed, such as including an RF sputtered zinc oxide layer (e.g., about 1450 nanometers thick), or including one or more other piezoelectric materials. In FIG. 4G, the unwanted portions of the piezoelectric region 414 can be lifted off or otherwise removed from the FBAR 400G. In an illustrative example, the piezoelectric region can include a crystallographic orientation (<002>) (e.g., indicating a strong c-axis piezoelectric crystal), such as confirmed through a sharp 34.4° peak in a 2θ X-ray diffraction pattern.

Figure 4H:
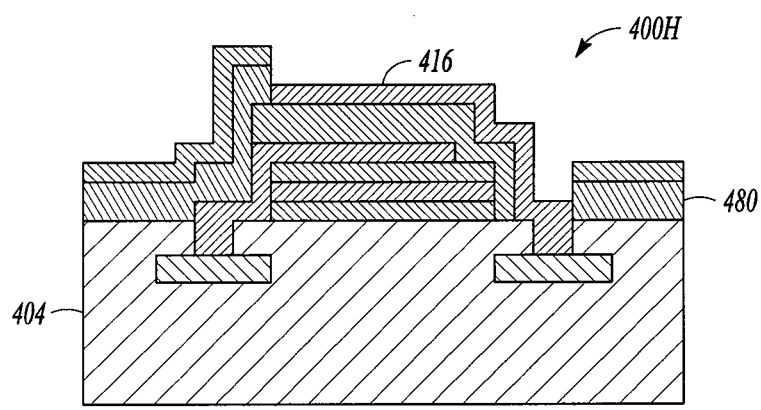
Figure 4I:
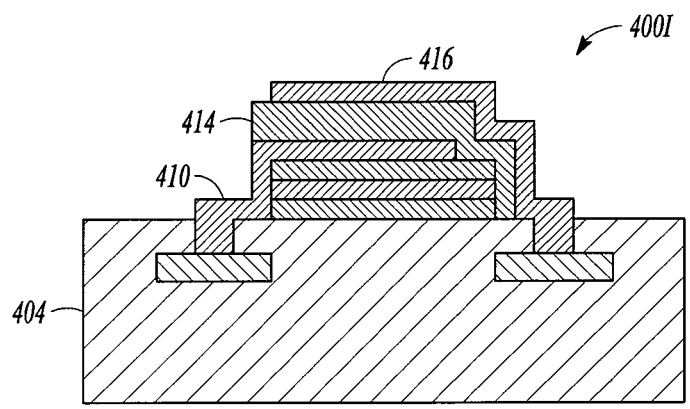

In FIG. 4H, the FBAR 400H can be patterned, and a top electrode 416 can be sputtered or otherwise deposited. In FIG. 4I, the unwanted portions of the top electrode 416 can be lifted off, or otherwise removed from the FBAR 400I. In an example, the top electrode 416 can include a top tungsten contact (e.g., about 200 nanometers thick) can be patterned and can connect through CMOS top metal to the underlying circuitry (e.g., an oscillator, amplifier, interconnect, or other circuitry elsewhere). In an example, the piezoelectric material can provide insulation in a lateral region of the FBAR 400G, such as to prevent electrical shorting between the top electrode 416, and one or more other regions, such as the mirror layer 410.

Figure 5:
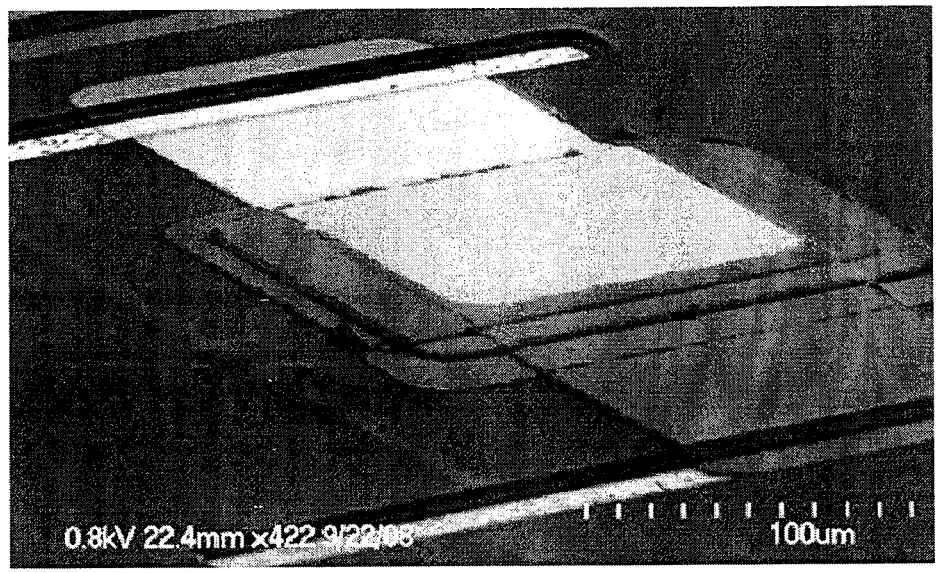
FIG. 5 includes an SEM micrograph of an illustrative example of a solidly-mounted monolithic FBAR, such as fabricated according to the processing of the examples of FIGS. 4A through 4I.

FIG. 5 includes an SEM micrograph of an illustrative example of a solidly-mounted monolithic FBAR, such as fabricated according to the processing of the examples of FIGS. 4A through 4I. In this illustrative example, a sensing surface of the FBAR can be about square, such as about 100 micrometers by 100 micrometers, with a corresponding array density (e.g., as shown in FIG. 6) limited primarily by the area of the individual FBAR sensors rather than any underlying circuitry.

Figure 6:
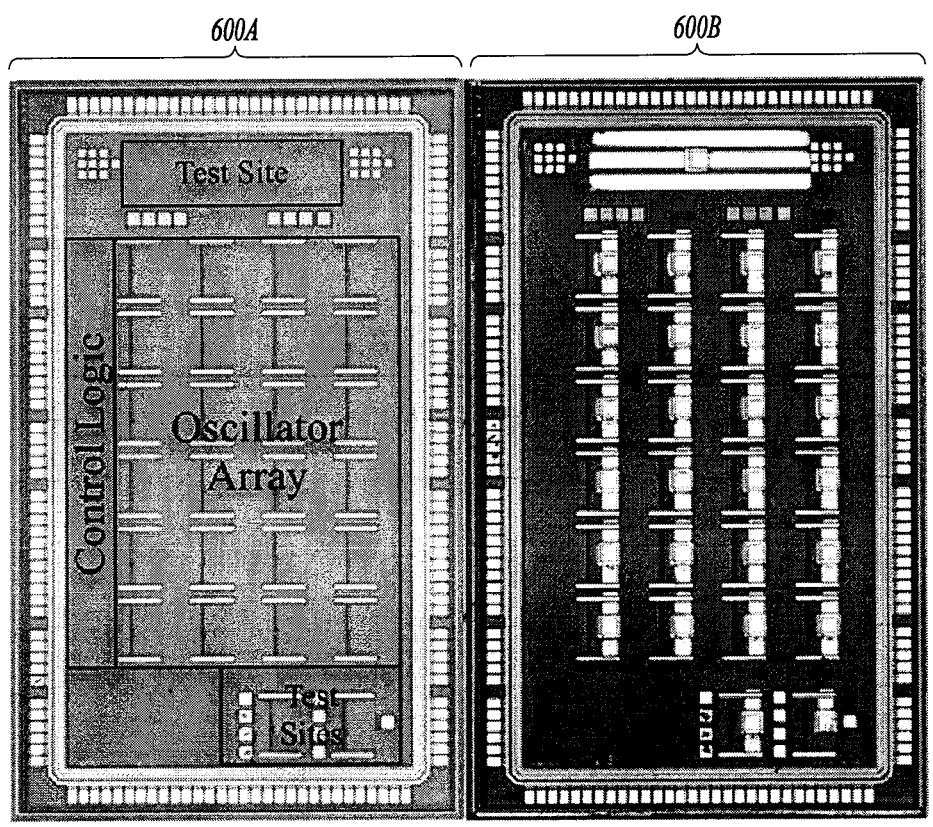
FIG. 6 includes two die photos of an illustrative example of a 6×4 array of FBAR-CMOS oscillators, including a first die photo after CMOS fabrication, and a second die photo after fabrication of the FBAR structures, such as fabricated according to the processing described in FIGS. 4A through 4I.

FIG. 6 includes two die photos of an illustrative example of a 6×4 array of FBAR-CMOS oscillators, including a first die photo 600A after CMOS fabrication but prior to fabrication of the FBAR structures, and a second die photo 600B after fabrication of the FBAR structures, such as fabricated according to the processing described in FIGS. 4A through I. In the illustrative example of the first die photo 600A, one or more test regions can be included on the die, such as for characterizing circuitry included in the die, or for testing one or more regions fabricated using similar materials or structures as used elsewhere in the array.

For example, in the second die photo 600B, the light bands near the top edge of the photo can include one or more passive test structures, such as for standalone testing of an active FBAR-CMOS oscillator or for testing of a passive FBAR resonator. Such testing can be used for characterization or calibration of one or more FBAR structures included in the array. In the illustrative example of the second die photo 600B, each FBAR-CMOS element in the array can occupy about 0.13 square millimeters, but it is believed that further optimization of the FBAR elements for particular sensing applications can lead to smaller FBAR footprints and a higher array density in certain implementations. In an illustrative example, such as the second die photo 600B, each FBAR-CMOS oscillator can include its own acoustic mirror, isolated from the surrounding oscillators, such as including one or more fabrication processes or structures such as shown and discussed above in FIG. 3, and FIGS. 4A through 4I. In another example, two or more FBAR structures can be formed or can incorporate a commonly-shared "blanket" acoustic mirror, such as formed or built up in a region underlying the two or more FBAR structures.

Figure 7A:
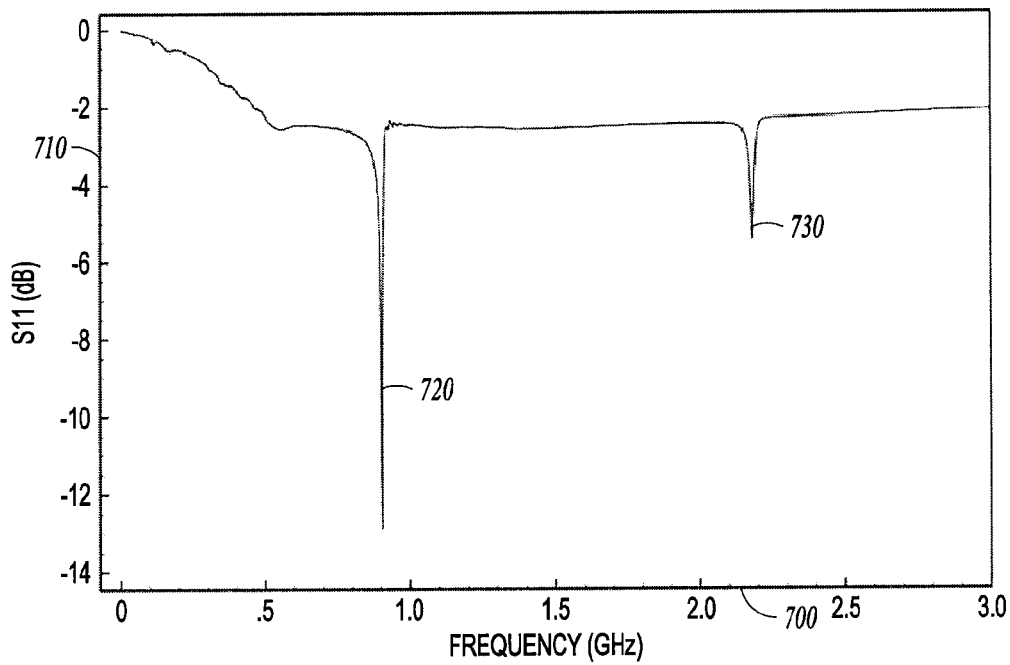
FIG. 7A through 7C illustrate generally illustrative examples of electrical performance of a single FBAR structure, fabricated on glass.
Figure 7B:
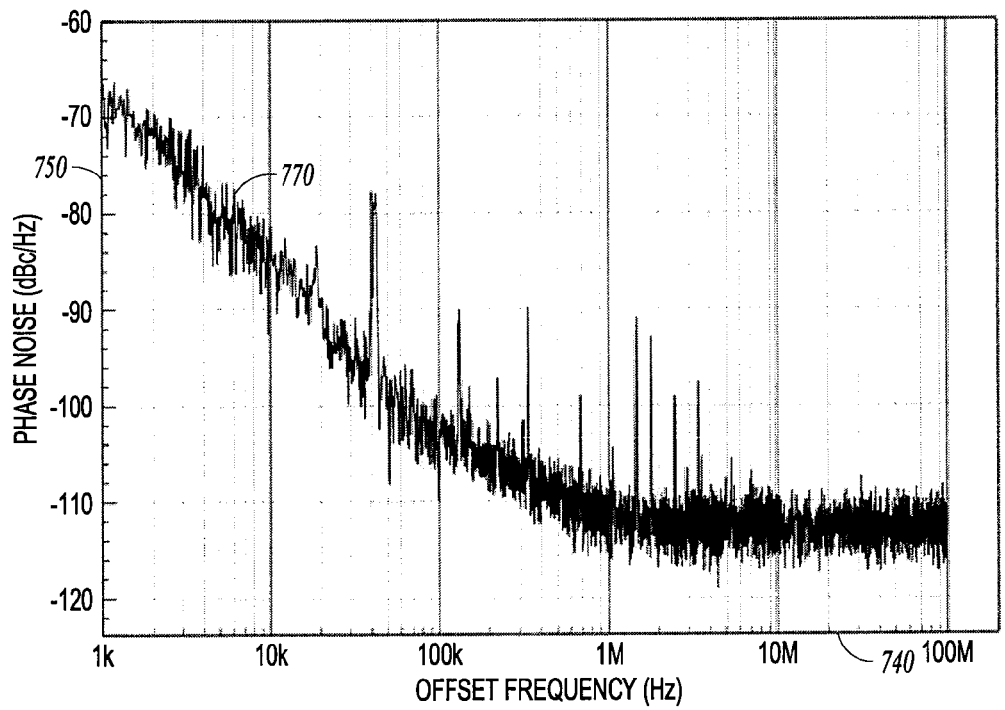
Figure 7C:
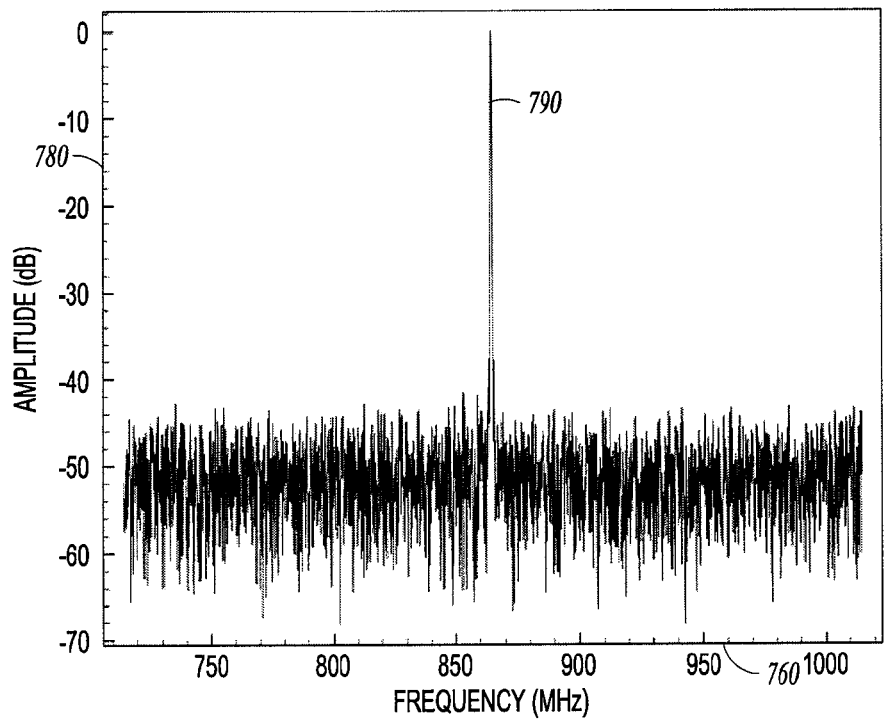

FIG. 7A-C illustrate generally illustrative examples of electrical performance of a single FBAR structure similar to the structure shown and discussed above in the examples of FIG. 3, and FIGS. 4A through 4I.

FIG. 7A shows an illustrative example of the S11 parameter 710 (e.g., proportional to the return loss, in dB) of the single FBAR plotted with respect to frequency 700 (in gigaHertz). In this illustrative example, the FBAR structure is fabricated on a glass substrate, including a blanketed acoustic mirror, and demonstrates a first resonance 720 at about $f_o$=905 megaHertz and a second resonance 730 at about 2.18 gigaHertz, which are believed to be attributable respectively to a shear and a longitudinal resonant mode of the FBAR, or might be attributable to excitation of a higher-order mode related to a resonance of the combined assembly. The second resonance 730 has not been observed in the integrated FBAR-CMOS device. The acoustic velocities of these modes share a near-identical ratio. Also, the resonant quality factor "Q," can be represented as $f_o/\Delta f$ (e.g., a "full-width half-maximum" or FWHM representation), and is approximately 113 for the first resonance 720 and approximately 129 for the second resonance 730. It is believed that correspondingly higher Qs might be achievable with better tuning of the acoustic mirror (e.g., to provide more effective reflection of acoustic energy or isolation between the resonator and the surrounding substrate).

FIG. 7B shows an illustrative example of the phase noise 750 (in dBc per Hertz), plotted with respect to an offset frequency 740 (in Hertz), of an FBAR-CMOS oscillator, including a measured noise of about −83 dBc/Hertz at an offset of 10 kiloHertz and about −104 dBc/Hertz at an offset of 100 kiloHertz, both measured from a carrier signal set at the fundamental frequency of oscillation. The relative slope regions of a phase noise plot 770 indicate a loaded Q for the oscillator of 218 in accordance with Leeson's phase noise relationship, where a knee in the plot 770 at $f_o/2Q$ can represent a transition to a relatively flat, white-noise dominated phase noise response. In an example, when the sensor is used to provide an input to a frequency counter, measurement integration (e.g., averaging or integrating multiple frequency or interval measurements during a specified measurement timeframe) can combat the effects of phase noise to improve measurement resolution.

FIG. 7C shows an illustrative example of the output amplitude spectrum 780 (plotted in dB), with respect to frequency 700 (in megaHertz) as measured at the output of one on-chip FBAR-CMOS oscillator, including a peak 790 at about 864.5 megaHertz. In an array, such as shown in the photos of FIG. 6, oscillators across array can demonstrate a spread of ~10 megaHertz in resonant frequency as compared to one another, such as due to variations in zinc oxide thickness, or other factors. However, this variation does not hinder differential mass measurements (e.g., measured at different times), such as where oscillation frequency is measured both before and after mass addition, since the mass sensitivity of the sensors can be relatively similar across the array (e.g., a similar offset in frequency occurs for a similar change in mass, independent of variation in a "baseline" resonant frequency).

Figure 8:
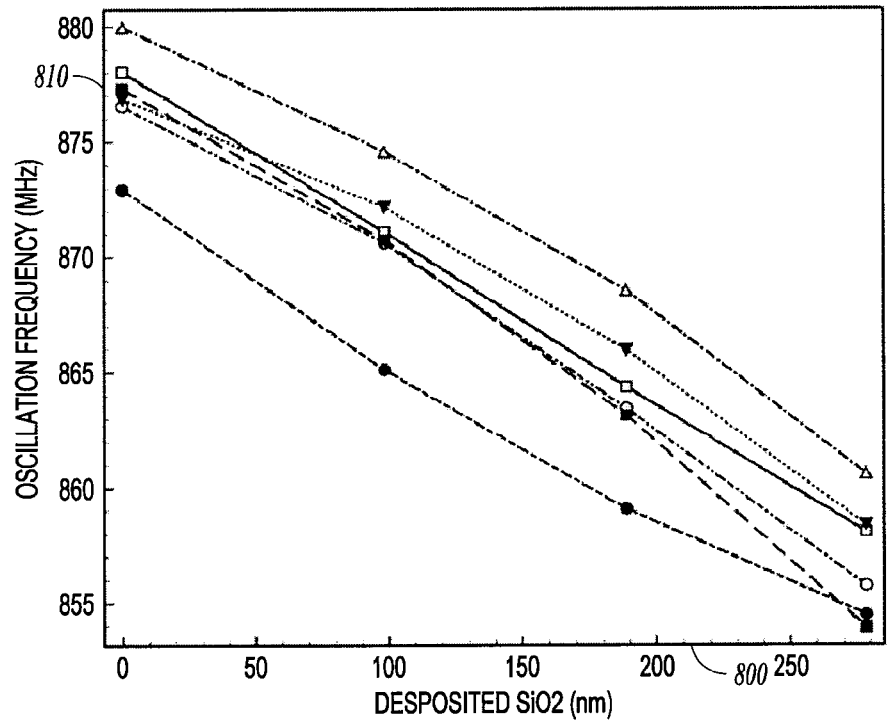
FIG. 8 illustrates generally an illustrative example of a plot of oscillation frequency versus a thickness of deposited silicon dioxide, such as for six different FBAR-CMOS oscillators included the 6×4 array of the example of FIG. 6.

FIG. 8 illustrates generally an illustrative example of a plot of an oscillation frequency 810 (in megaHertz) versus a thickness 800 (in nanometers) of deposited silicon dioxide, such as for six different FBAR-CMOS oscillators included a 6×4 array of the example of FIG. 6. In this illustrative example, the fundamental oscillation frequencies of each of the six oscillators can be measured first as a baseline, after which mass can be added (e.g., by forming successive layers of patterned silicon dioxide, RF sputtered onto the FBAR top surfaces, such as a sensing surface). Frequency measurements can then be taken after each addition of mass, such as emulating the field behavior of such sensors as mass accretes or binds to a corresponding functionalized sensing surface. In this illustrative example, all oscillators that completed the mass series are shown, while those not depicted failed either before or during the testing process (e.g., did not sustain measurable oscillation). The frequency sensitivity of an FBAR to mass additions (e.g., change in frequency per unit mass addition) can be represented by the Sauerbrey equation, as $\Delta f = -(f_o^2 \Delta m/NA\rho)$, where $f_o$ can represent the operating frequency, $\Delta m$ can represent the mass addition, N can represent a sensitivity constant, A can represent the active area, and $\rho$ can represent the density. The Sauerbrey equation predicts a linear change in frequency for small additions of uniform-thickness mass, similar to the responses shown in the illustrative example of FIG. 8, with the average mass sensitivity of the examples of FIG. 8 representing about $3.05 \times 10^{-12}$ grams/Hertz centimeter$^2$, which is well above the sensitivity of a typical QCM (about $6 \times 10^{-9}$ grams/Hertz centimeter$^2$) and comparable to off-chip FBAR sensors.

Figure 9:
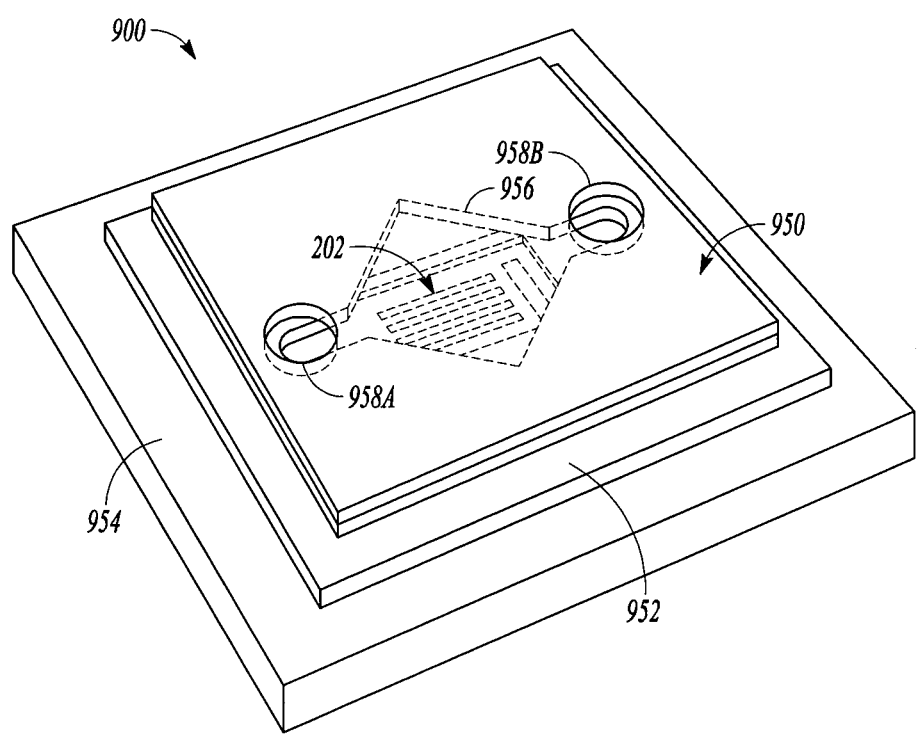
FIG. 9 illustrates generally an illustrative example of an apparatus comprising a fluid reservoir including a cavity coupled to an FBAR-CMOS resonator array.

FIG. 9 illustrates generally an illustrative example of an apparatus 900 that can include a fluid reservoir, such as including a cavity region 956. In an example, the fluid reservoir can be mechanically (e.g., anchored or fluidically coupled) to an FBAR-CMOS resonator array 202.

In an example, first layer 950 can include a first fluid access port 958A and a second fluid access port 958B. The first layer 950 can be fabricated such as comprising a polyester flow channel overlay assembly, or including one or more other materials or assemblies. A second layer can be mechanically coupled between the first layer 950 and one or more other regions, such as including polyester or one or more other materials.

In an example, the second layer can be located between the first layer 950 and an integrated circuit encapsulant 952 (e.g., an epoxy encapsulant or including one or more other materials), another portion of an integrated circuit package, an integrated circuit substrate, an interposer printed circuit assembly 954, or one or more other portion of the apparatus 900. For example, the interposer printed circuit assembly 954 can include one or more interconnects such as between the FBAR-CMOS array 202 and a ball-grid array (BGA) included as a portion of the interposer printed circuit assembly 954. In an example, one or more of the first or second fluid access ports 958A or 958B can be aligned with corresponding channels or other fluidic pathways, such as configured to provide fluidic coupling of an analyte to the cavity region 956 via one or more of the first or second fluid access ports 958A or 958B.

In an example, the cavity region can be located near an FBAR-CMOS resonator array (e.g., above as in the illustrative example of FIG. 9, or elsewhere), and the resonator array can be configured for use in point-of-care detection of a presence or quantity of an analyte, such as for diagnostic use in detection of cardiac biomarkers, or for one or more other detection or diagnostic purposes such as discussed in the examples above.

In an example, the apparatus 900 can be included as a portion of a "cartridge" or other assembly, such as can be disposable. For example, as shown in FIG. 9, a microfluidic or other fluid delivery layer can be combined with the sensor array 202, such as to provide an enzyme-linked immunosorbent assay (ELISA)-comparable protein quantification in a disposable cartridge on finger-stick blood volumes.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, comprising:
a thin-film bulk acoustic resonator comprising:
an acoustic mirror;
a piezoelectric region acoustically coupled to the acoustic mirror;
a first conductor electrically coupled to the piezoelectric region; and
a second conductor electrically coupled to the piezoelectric region and electrically insulated from the first conductor;
a CMOS integrated circuit substrate including an interface circuit, the first and second conductors electrically coupled to the interface circuit;
wherein the thin-film bulk acoustic resonator is solidly-mounted to the CMOS integrated circuit substrate along an entire surface of the resonator,
wherein the thin-film bulk acoustic resonator is monolithically integrated to the CMOS integrated circuit substrate;
wherein the integrated circuit substrate is configured to mechanically support the resonator; and
wherein the acoustic mirror is configured to inhibit or prevent coupling of acoustic energy from the piezoelectric region into the integrated circuit substrate at or near a resonant frequency of the thin-film bulk acoustic resonator.

2. The apparatus of claim 1, wherein the piezoelectric region comprises zinc oxide.

3. The apparatus of claim 1, wherein the acoustic mirror comprises alternating layers of tungsten and silicon dioxide.

4. The apparatus of claim 3, wherein the resonator is located on a top surface of the integrated circuit.

5. The apparatus of claim 1, comprising an oscillator including the acoustic resonator and at least a portion of the interface circuit.

6. The apparatus of claim 5, wherein an operating frequency of the oscillator is determined at least in part by a mass loading the piezoelectric region.

7. The apparatus of claim 6, wherein the resonator comprises a sensing surface configured to detect at least one of a specified protein binding, a specified antibody-antigen coupling, a specified hybridization of a DNA oligomer, or an adsorption of specified gas molecules.

8. The apparatus of claim 7, wherein the sensing surface is functionalized to adsorb gas molecules.

9. The apparatus of claim 7, wherein the sensing surface includes an immobilized antibody, an antibody fragment, or a nucleic acid probe.

10. The apparatus of claim 7, wherein the sensing surface is configured to increase in mass in response to at least one of a specified protein binding, a specified antibody-antigen coupling, a specified hybridization of a DNA oligomer, or an adsorption of specified gas molecules.

11. The apparatus of claim 5, wherein the oscillator is configured to operate using a shear mode of mechanical oscillation of the resonator.

12. The apparatus of claim 5, wherein the oscillator is configured to oscillate at the specified operating frequency when the apparatus is in contact with or surrounded by a liquid medium.

13. The apparatus of claim 5, wherein the integrated circuit comprises a frequency counter coupled to the oscillator and configured to provide information indicative of an oscillation frequency of the oscillator.

14. An apparatus, comprising:
a thin-film bulk acoustic resonator array, each resonator comprising:
an acoustic mirror;
a piezoelectric region acoustically coupled to the acoustic mirror;
a first conductor electrically coupled to the piezoelectric region; and
a second conductor electrically coupled to the piezoelectric region and electrically insulated from the first conductor;
a CMOS integrated circuit substrate including an interface circuit, the first and second conductors of each resonator electrically coupled to the interface circuit;
wherein the thin-film bulk acoustic resonator array is solidly-mounted to the CMOS integrated circuit substrate along an entire surface of the resonator,
wherein the thin-film bulk acoustic resonator is and monolithically integrated to the CMOS integrated circuit substrate;
wherein the integrated circuit substrate is configured to mechanically support the resonator array;
wherein each respective acoustic mirror is configured to reduce or inhibit coupling of acoustic energy from the respective piezoelectric region into the integrated circuit substrate at or near a resonant frequency of the respective thin-film bulk acoustic resonator including the respective acoustic mirror; and
wherein the array comprises an array of oscillators, each oscillator including at least one acoustic resonator and at least a portion of the interface circuit.

15. The apparatus of claim 14, wherein an operating frequency of each oscillator is determined at least in part by a mass loading each piezoelectric region.

16. The apparatus of claim 14, wherein the integrated circuit comprises a frequency counter coupled to at least one oscillator included in the array, and configured to provide information indicative of an oscillation frequency of the at least one oscillator.

17. The apparatus of claim 14, wherein each piezoelectric region comprises zinc oxide.

18. The apparatus of claim 14, wherein each acoustic mirror comprises alternating layers of tungsten and silicon dioxide.

19. The apparatus of claim 14, wherein each resonator is located on a top surface of the integrated circuit.

20. The apparatus of claim 15, wherein at least one oscillator included in the array includes a resonator comprising a sensing surface that is configured to detect at least one of a specified protein binding, a specified antibody-antigen coupling, a specified hybridization of a DNA oligomer, or an adsorption of specified gas molecules.

21. The apparatus of claim 20, wherein the sensing surface is functionalized to adsorb gas molecules.

22. The apparatus of claim 20, wherein the sensing surface includes an immobilized antibody, an antibody fragment, or a nucleic acid probe.

23. The apparatus of claim 20, wherein the sensing surface is configured to increase in mass in response to at least one of a specified protein binding, a specified antibody-antigen coupling, a specified hybridization of a DNA oligomer, or an adsorption of specified gas molecules.

24. The apparatus of claim 14, wherein each oscillator is configured to operate using a shear mode of mechanical oscillation of each resonator.

25. The apparatus of claim 14, wherein each oscillator is configured to oscillate at the specified operating frequency when the apparatus is in contact with or surrounded by a liquid medium.

* * * * *

UNITED STATES PATENT AND TRADEMARK OFFICE
CERTIFICATE OF CORRECTION

Page 1 of 1

PATENT NO.        : 9,255,912 B2
APPLICATION NO.   : 13/283670
DATED             : February 9, 2016
INVENTOR(S)       : Matthew Johnston, Kenneth Shepard and Ioannis Kymissis It is certified that error appears in the above-identified patent and that said Letters Patent is hereby corrected as shown below:

Specification

STATEMENT REGARDING FEDERALLY SPONSORED RESEARCH OR DEVELOPMENT:

Col. 1, ln. 25: Statement Regarding Federally Sponsored Research or Development: "This invention was made with government support under award number U01ES016074 from National Institute of Environmental Health Sciences or the National Institutes of Health. The government has certain rights in this invention." should read:

-- This invention was made with government support under ES016074 awarded by the National Institutes of Health. The government has certain rights in this invention. --

Signed and Sealed this
Twenty-eighth Day of June, 2016

Michelle K. Lee
*Director of the United States Patent and Trademark Office*